United States Patent [19]
Andersen

[11] Patent Number: 5,556,385
[45] Date of Patent: Sep. 17, 1996

[54] IMPROVED PERCUTANEOUS ACCESS DEVICE

[75] Inventor: Erik Andersen, Gurnee, Ill.

[73] Assignee: Corpak, Inc., Wheeling, Ill.

[21] Appl. No.: 349,897

[22] Filed: Dec. 6, 1994

[51] Int. Cl.$^6$ .................................. A61M 29/00
[52] U.S. Cl. .............. 604/174; 604/96; 604/247
[58] Field of Search ............. 604/96, 178, 105, 604/175, 174, 280, 167, 265, 93, 33, 49, 52, 27, 28, 30, 34, 170, 29, 244, 247, 256, 332, 337, 43, 45, 54, 104, 277, 334, 335, 338; 600/32, 29

[56] References Cited

U.S. PATENT DOCUMENTS

| | | |
|---|---|---|
| 4,315,513 | 2/1982 | Nawash et al. . |
| 4,344,434 | 8/1982 | Robertson . |
| 4,393,873 | 7/1983 | Nawash et al. . |
| 4,668,225 | 5/1987 | Russo et al. ............... 604/280 |
| 4,685,901 | 8/1987 | Parks ........................ 604/96 |
| 4,834,713 | 5/1989 | Suthanthiran . |
| 4,863,438 | 9/1989 | Gauderer et al. . |
| 4,900,306 | 2/1990 | Quinn et al. . |
| 4,944,732 | 7/1990 | Russo ........................ 604/105 |
| 5,007,900 | 4/1991 | Picha et al. . |
| 5,026,352 | 6/1991 | Anderson . |
| 5,057,093 | 10/1991 | Clegg et al. . |
| 5,059,170 | 10/1991 | Cameron . |
| 5,071,405 | 12/1991 | Piontek et al. ............... 604/96 |
| 5,092,850 | 3/1992 | Buma . |
| 5,114,398 | 5/1992 | Trick et al. ............... 604/96 |
| 5,125,897 | 6/1992 | Quinn et al. . |
| 5,234,417 | 8/1993 | Parks et al. . |
| 5,250,040 | 10/1993 | Parks et al. . |
| 5,267,969 | 12/1993 | Hirsch et al. . |
| 5,336,203 | 8/1994 | Goldhardt et al. . |
| 5,342,321 | 8/1994 | Potter ....................... 604/96 |

*Primary Examiner*—Corrine M. McDermott
*Assistant Examiner*—N. Kent Gring
*Attorney, Agent, or Firm*—Wallenstein & Wagner, Ltd.

[57] ABSTRACT

A device for percutaneous administration of fluid preparations into a body cavity, vessel or organ, the device including a tube having both a fluid lumen and an inflation lumen and defined by a proximal end lying outside of the body and a distal end lying within the body, the proximal end of the fluid lumen being in fluid communication with a fluid source and the distal end disposed within the body, the distal end of the inflation lumen in communication with an inflatable member disposed within the body. In one embodiment, one end of the tube is connected to a retention platform having a central portion with a recess to confront the patient's abdominal wall. The retention platform has a plurality of circumferentially-spaced fingers extending radially from said central portion where only the end portion of each finger rests on the abdominal wall of the patient. Preferably, the proximal end of the inflation lumen is remote from the fluid lumen. The device also preferably utilizes a flexible band extending from the retention platform, which carries a plug for sealing the proximal end of the fluid lumen.

10 Claims, 2 Drawing Sheets

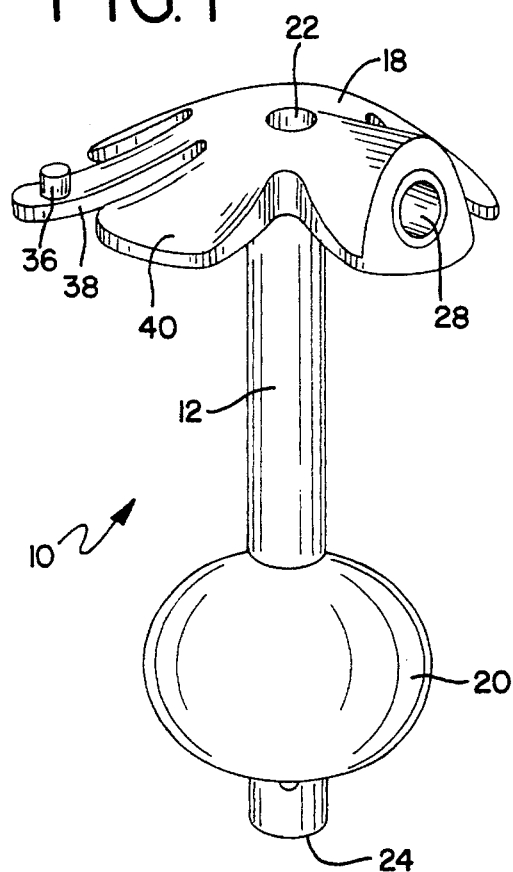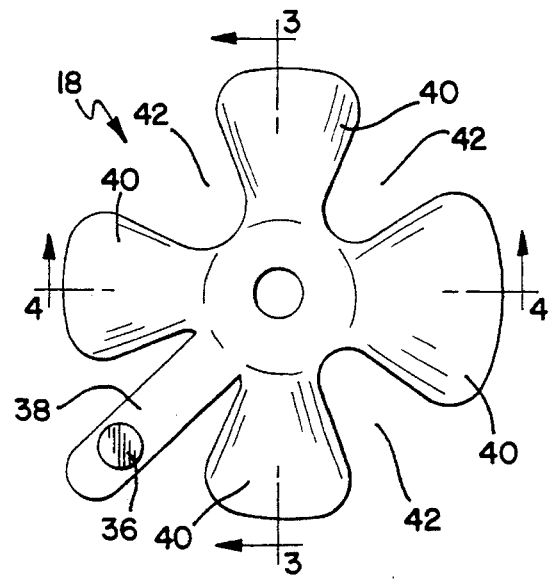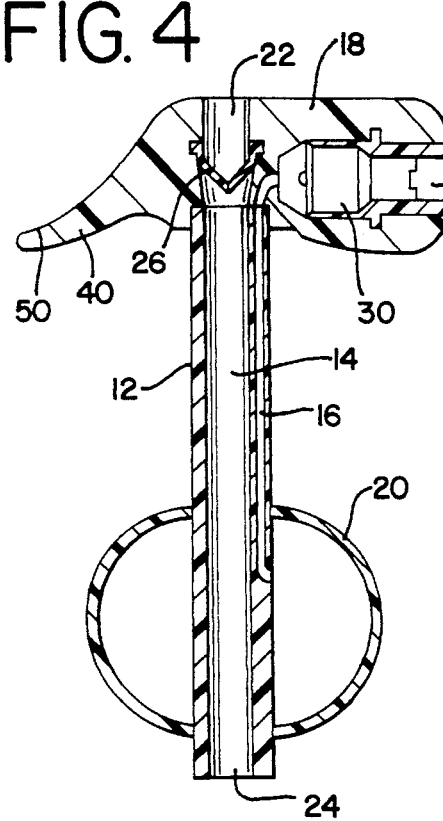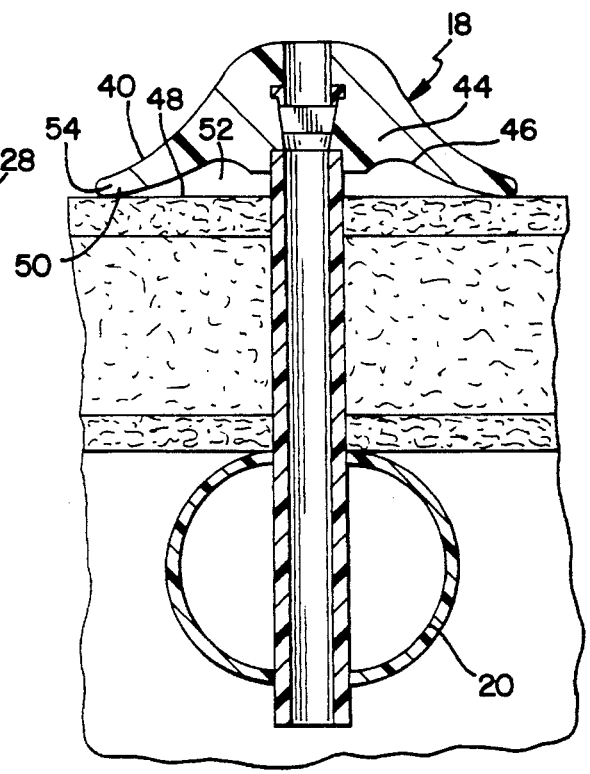

5,556,385

IMPROVED PERCUTANEOUS ACCESS DEVICE

TECHNICAL FIELD

The present invention generally relates to devices used for percutaneous administration of fluids into a body cavity, vessel or organ.

BACKGROUND OF THE INVENTION

Numerous medical procedures involve percutaneous administration of fluids into, or removal of fluids from, a patient's body. Percutaneous access devices are typically used in performing these medical procedures and provide access into a patient's body cavity, vessel or organ. Such percutaneous access devices include, among other things, devices for gastrostomy, jejunostomy, angioplasty, and peritoneal dialysis. Often times, it is desirable for such percutaneous access devices to have a portion outside the patient's body which helps retain the device in place and provides a means of attaching medical tubing. As will be explained, there is a need for the external portion to have a low profile, and for the percutaneous access device to have minimal contact with the patient's skin to reduce irritation to the skin and allow ease of access to the skin underlying the device for cleaning. Also, there is a need for a percutaneous access device having suitable differentiation between its multiple tubes or fluid ports.

As an example, and to further describe the background of the invention, one type of commonly used percutaneous access device is the gastrostomy device. For patients having chronic or acute nutritional needs, percutaneous enteral feeding through a stoma, such as a gastrostomy, is often necessary. The gastrostomy is typically formed through use of a percutaneous endoscopic technique and intubated with a gastrostomy tube to effect enteral feeding.

After initial formation and intubation of the gastrostomy, it is often necessary to replace the gastrostomy tube with a device more suitable to long-term feeding needs. It is preferable for these devices to have a low structural profile located closely to the patient's skin outside of the abdominal wall, without discomfort or undue bulging or snagging of clothing. A gastrostomy tube includes a feeding lumen and an inflation lumen. The feeding tube has a proximal end that connects to a nutrient source, and a distal end disposed within the patient. The inflation lumen has one proximal end that connects to an inflation medium source, such as pressurized fluid or air, and another end in communication with an inflatable retention member. The inflatable retention member is located inside the patient's stomach, where it is inflated by connection to an inflation medium source through the inflation tube, for anchoring and retaining the distal end of the gastrostomy tube within the stomach. To retain the device close to the outer abdominal wall of the patient, a retention platform is used, which typically has been a flat disk-shaped member. The disk-shaped member is connected to the tube portion of the device and is positioned flush against the patient's skin. When the device is not in use for enteral feeding, a closure is provided to seal the feeding tube.

An example of one prior art gastrostomy device is found in U.S. Pat. No. 5,125,897. The device disclosed in this patent includes a retention platform which, upon intubation, rests on the abdominal wall of the patient to secure the device. Means are provided to seal the feeding tube when it is not in use. U.S. Pat. No. 4,863,438 shows another gastrostomy device having a type of retention platform utilizing a pair of short flat wings integrally molded on the outer end of the tube, to make the tube self-retaining and flush up against the skin. If skin irritation should occur, the wings can be rotated a part-turn to different areas of the skin. U.S. Pat. No. 4,315,513 shows a gastrostomy device utilizing a retention platform which is a flat disk-shaped member. The surface of the retention platform which faces the skin is provided with a set of raised ridges arranged in spoke-like fashion. The raised ridges maintain the retention platform slightly spaced away from the outer abdominal wall to permit the entry of air between the skin and retention platform.

There are many problems associated with the prior art percutaneous access devices, such as the prior art gastrostomy devices. One such problem with some devices is that, when the device is inserted into the patient for an extended period, the retention platform is in constant contact with the skin where it often causes discomfort to the patient. The retention platforms in most devices are generally flat, and thus a significant portion of the surface area of the platform contacts the skin. As a result, the skin can become irritated due to the lack of air ventilation to the portion of skin next to the retention platform. Although some retention platforms have been designed with orifices to help ventilate the skin underlying the retention platform, such ventilation has been less than desirable, as skin irritation can still occur. In addition, the skin underlying the retention platform cannot be adequately ventilated or cleaned when the retention platform sits closely against the skin of the patient.

Another problem occurs when the percutaneous medical procedure is performed, such as when the feeding process is initiated with a gastrostomy device. Users potentially confuse the inflation tube inlet port for the feeding tube inlet port because they are located in close proximity to one another. As a result, the inflation tube inlet can be erroneously connected with the nutrient source, so that the inflatable retention member is filled with food. In such a case, the inflatable retention member eventually bursts inside the stomach of the patient. The gastrostomy device must then be removed from the patient and a new gastrostomy device inserted. This is expensive, inconvenient and painful to the patient.

Hence, prior to the development of the present invention, a need existed for a percutaneous access device which addresses the problems associated with the prior art devices.

SUMMARY OF THE INVENTION

An improved device for percutaneous administration of fluids has been developed which solves the problems of prior art devices. The present invention includes a tube having both a fluid lumen and an inflation lumen and defined by a proximal end lying outside of the body and a distal end lying within the body. The proximal end of the fluid lumen is in fluid communication with a fluid source and the distal end is disposed within the body. The distal end of the inflation lumen is in communication with an inflatable member which is disposed within the body. In accordance with one of the features of the invention, the device includes a retention platform having a central portion with a recess which confronts the patient's skin. The retention platform receives one end of the tube and rests on the patient's skin.

In accordance with a specific aspect of the invention, the recess of the central portion is of a general arcuate-shaped cross-section. The arcuate shape provides an appreciable space above the skin to allow for constant air ventilation through the retention platform to the underlying skin. The retention platform preferably has a plurality of circumferentially-spaced fingers extending radially from the central portion of the platform. There are spaces between the fingers which, along with the central recessed portion of the retention platform, allow for greater access for air ventilation and for cleaning the underlying skin. The fingers of the retention platform preferably include a curled-end portion, such that only a portion of the end contacts the skin. This lessens skin irritation because less skin is contacted by the retention platform.

In accordance with another feature of the invention, the proximal end of the inflation lumen is remote from the fluid lumen. In prior art devices, the inflation lumen and fluid lumen are in close proximity to one another at the proximal end of the tube. In the preferred form of the present invention, the proximal end of the inflation lumen is remote from the proximal end of the fluid lumen on the retention platform. Preferably, the proximal end of the inflation lumen is generally parallel to the patient's skin, while the proximal end of the fluid lumen is generally transverse to the patient's skin and the inflation lumen. This reduces the chances of a user confusing the fluid lumen with the inflation lumen, and reduces the unfavorable chance of filling the inflation tube with fluid preparation. This design also provides a lower profile of the retention platform, as the proximal end of the inflation lumen does not extend far above the retention platform.

In accordance with another feature of the invention, a flexible band preferably carries a plug to close the fluid lumen at its proximal end. The flexible band, extending radially from the center of the retention platform, folds once along its length allowing the plug to be inserted into the end of the fluid lumen when the fluid preparation is not being administered. This configuration also reduces the chances of a user confusing the fluid lumen with the inflation lumen.

Other advantages and aspects of the invention will become apparent upon making reference to the specification, claims, and drawings to follow.

BRIEF DESCRIPTION OF THE DRAWINGS

FIG. 1 is a perspective view of one embodiment of the present invention;

FIG. 2 is a plan view of one embodiment of the present invention;

FIG. 3 is a cross-sectional view taken along line 3—3 of the device shown in FIG. 2;

FIG. 4 is a cross-sectional view taken along line 4—4 of the device shown in FIG. 2;

DETAILED DESCRIPTION OF THE INVENTION

Figure 5:
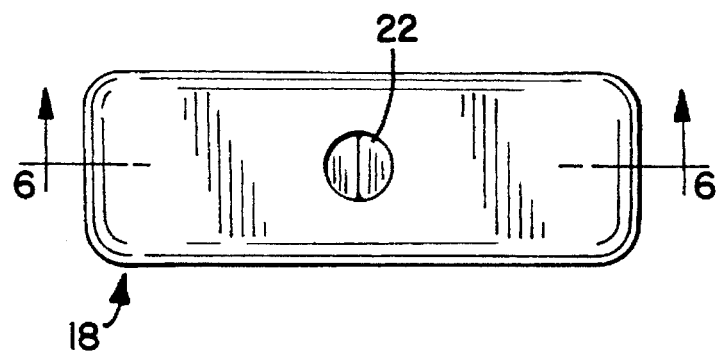
FIG. 5 is a plan view of an alternative embodiment of the present invention; and, FIG. 6 is a cross-sectional view taken along line 6—6 of the device shown in FIG. 5.

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated.

Referring now to the drawings, FIG. 1 discloses a preferred embodiment of a percutaneous access device 10 of the present invention. The tube 12 houses both a fluid lumen 14 and an inflation lumen 16 as seen in the cross-sectional view in FIG. 4. The proximal end of the tube 12 passes through the center of a retention platform 18. The distal end of the tube 12 extends downwardly through an inflatable retention member 20 and into the patient's body.

As seen in FIG. 4, the fluid lumen 14 has a fluid inlet port 22 near the center of the retention platform 18, where a fluid source may be connected to effect the fluid administration into the patient. The fluid lumen 14 passes through the length of the tube 12, through the inflatable retention member 20. At the distal end, the tube has an outlet 24, disposed into the patient's body cavity, vessel or organ, to convey fluid preparations into the patient. The fluid lumen 14 includes a one-way anti-reflux valve 26, preferably a duckbill valve, which prevents reflux of fluid.

As seen in FIG. 1, an inflation port 28 is provided for the inflation lumen 16. As seen in FIG. 4, the inflation lumen 16 is in communication with the inflatable retention member 20. A one-way valve 30 is provided near the inflation port 28 to maintain pressure once the retention member 20 is inflated.

As best seen in FIG. 2, the retention platform 18 has fingers 40 circumferentially-spaced which extend radially from the central portion of the retention platform 18. There are spaces 42 between the fingers 40 which improve air circulation to the patient's skin underlying the retention platform 18.

The prior art retention platforms are generally flat and do not allow for adequate air ventilation to the patient's skin. As best shown in FIG. 3, the present invention utilizes a retention platform 18 having a central portion 44 with a recess 46 which confronts the patient's skin 48. Rather than a significant portion or entire face of the retention platform 18 contacting the skin, only a portion of the retention platform 18 contacts the skin 48. This reduces skin irritation by increasing air ventilation and reducing the surface area of the retention platform 18 which comes in contact with the skin.

FIG. 3 best shows the central portion 44 with a recess 46 which confronts the patient's skin 48. In its preferred form, the recess 46 of the central portion 44 is of an arcuate-shaped cross-section. It should be understood that the central portion 44, with a recess 46 which confronts the patient's skin 48, can be created by a number of configurations and not limited to an arcuate shape.

The central portion 44 with a recess 46 which confronts the patient's skin 48 assures that a constant air space 52 is maintained between the retention platform 18 and the patient's skin 48. Although some prior art retention platforms have ridges which may maintain part of the platform a slight distance above the patient's skin, they are still designed flat. The recess 46 of the present invention provides air ventilation and assures that the minimum amount of surface area of the retention platform 18 will contact the skin. The central portion 44 with a recess 46 which confronts the patient's skin, along with the space 42 between the fingers 40, also allows for cleansing the patient's skin under the retention platform 18, which cannot be achieved with the flat retention platforms.

The surface area of the retention platform 18 that comes in contact with the skin 48 is further reduced by the upward curl 50 of the end portion of each finger 40 of the retention platform 18. This upward curl 50, along with the rounded edges 54 of each finger, best seen in FIG. 3, assure that the device does not protrude into the patient's skin. These features of the present device lessen skin irritation three-fold by assuring constant air ventilation to the patient's skin 48 underlying the retention platform 18, allowing access between the fingers 40 for cleansing the underlying skin 48 and minimizing the surface area of the retention platform 18 contacting the patient's skin 48.

FIG. 3 illustrates a cross-sectional view of intubation of the percutaneous access device 10. In a configuration not shown, the retention member 20 is in a deflated state so as to facilitate insertion into the stoma in the patient's body. After insertion of the percutaneous access device 10, the retention member 20 is inflated through the air inflation lumen 16. This retains the percutaneous access device 10 in the patient's body. The retention platform 18 rests on the patient's skin 48.

Unlike the prior art devices which locate the inflation port of the inflation lumen 16 in close proximity to the fluid inlet port 22 of the fluid lumen 14, the present invention causes the inflation port 28 to be remote from the fluid inlet port 22. As seen in FIGS. 1 and 4, the fluid inlet port 22 is located on the central portion of the retention platform 18. The inflation port 28 extends a remote distance from the fluid inlet port 22. Also, the proximal end of the inflation lumen 16 preferably is generally parallel to the patient's skin 48, while the fluid inlet port 22 is preferably generally transverse to the patient's skin 48. This reduces the chances of a user confusing the inflation port 28 for the fluid inlet port 22 and filling the inflatable retention member 20 with fluid preparation. If this occurs, the inflatable retention member 20 bursts inside the patient and the device must then be replaced.

A plug 36 carried on the distal end of flexible band 38 may be inserted into the fluid inlet port 22 providing a secure closure for the fluid lumen 14. In this configuration, when percutaneous administration of fluids is not taking place, the plug 36 is inserted into the fluid inlet port 22. This further reduces confusion between the fluid inlet port 22 and the inflation port 28.

Figure 6:
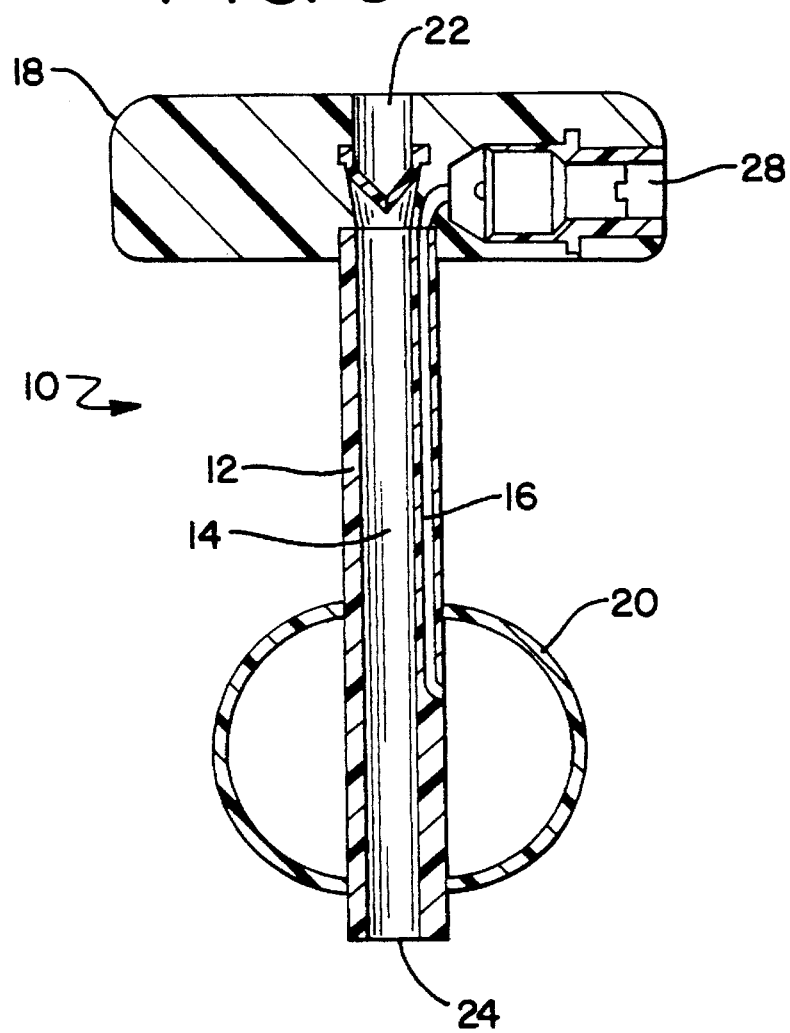

FIGS. 5 and 6 illustrate another embodiment of the invention. Although this embodiment does not utilize a retention platform having a central portion 44 with a recess 46 which confronts the patient's skin, it does utilize a design where the inlet port is remote from the fluid inlet port. FIGS. 5 and 6 show the percutaneous access device 10 having a tube 12 and generally flat retention platform 18. FIG. 6 shows a cross-section of the percutaneous access device 10 taken along line 6—6 of FIG. 5. The gastrostomy tube 12 houses a fluid lumen 14 and an inflation lumen 16. The proximal end of the fluid lumen is generally transverse to the patient's skin (not shown) and the inflation lumen 16. The inflation port 28 is remote from the fluid inlet port 22, as it is located at one side of the retention platform 18, and the inflation lumen is generally parallel to the patient's skin. As with the embodiment in FIGS. 1–4, the remote location of the inflation port 28 and the fluid inlet port 22 reduces the chances of a user confusing the inlet ports.

While the invention has been described with reference to a preferred embodiment, it will be understood by those skilled in the art that various changes may be and equivalents may be substituted for elements thereof without departing from the broader aspects of the invention. Also, it is intended that broad claims not specifying details of particular embodiment disclosed herein as the best mode contemplated for carrying out the invention should not be limited to such details.

I claim:

1. In a device for percutaneous administration of fluids from a fluid source into a body cavity, vessel or organ of a patient, the device including a tube having a fluid lumen, an inflatable member and an inflation lumen and defined by a proximal end lying outside of the patient and a distal end lying within the patient, the proximal end of the fluid lumen being in fluid communication with the fluid source and the distal end disposed within the patient, the proximal end of the inflation lumen in communication with the inflatable member disposed within the patient, the improvement comprising:

a retention platform disposed about the proximal end of the cube, the platform having an underside surface with a raised central portion defining a recess which is generally arcuate-shaped and which occupies a major portion of the extent of the platform;

said retention platform having a plurality of circumferentially-spaced fingers extending radially outward from the proximal end of the tube, the circumferentially-spaced fingers having a width which increases as said fingers extend outward;

the platform making contact with the patient only on peripheral edge portions of the circumferentially-spaced fingers.

2. The device of claim 1 wherein said proximal end of said inflation lumen is in communication with an inflation port of the retention platform which is positioned perpendicular to said tube and fluid lumen.

3. The device of claim 1 wherein the fingers have a rounded end portion.

4. The device of claim 1 where said fingers have an end portion which curls away from said recess of the central portion.

5. In a percutaneous access device adapted for administration of fluids from a fluid source into a body cavity, vessel or organ of a patient, the device including a tube having a fluid lumen, an inflatable member and an inflation lumen and defined by a proximal end lying outside of the patient and a distal end lying within the patient, the proximal end of the fluid lumen being in fluid communication with the fluid source and the distal end disposed within the body, the proximal end of the inflation lumen in communication with the inflatable member disposed within the body, the improvement comprising:

the proximal end of the inflation lumen being generally perpendicular to the tube and the proximal end of the fluid lumen.

6. The device of claim 5 having a retention platform with a central portion having a distal surface with a recess occupying a major portion of its extent and which is of a generally arcuate-shaped cross-section to confront the patient in spaced relation thereto and a peripheral portion contacting the patient;

said retention platform having a plurality of circumferentially-spaced fingers extending radially outward from the proximal end of the tube, said circumferentially-spaced fingers making contact with the patient only at said peripheral portions.

7. A percutaneous access device adapted for administration of fluids from a fluid source into a body cavity, vessel or organ of a patient, comprising:

a tube having a fluid lumen and an inflation lumen and defined by a proximal portion and a distal portion;

an inflatable member at the distal portion of the tube and in fluid communication with said inflation lumen;

an inflation port integral with the inflation lumen and aligned generally perpendicular to said tube;

a retention platform disposed about the proximal portion of said tube and having a plurality of circumferentially-spaced fingers which extend radially outward from the proximal portion of the tube and an underside surface facing toward said distal end of said tube;

said underside surface of the retention platform having a recess of generally arcuate shape; and said fingers having a width which increases as said fingers extend outward.

8. The percutaneous access device of claim 7 wherein said inflation port passes through one of said fingers.

9. The percutaneous access device of claim 1, 5 or 7 wherein a plug is integrally attached to said platform, said plug insertable into the fluid lumen at said proximal portion of the tube.

10. The percutaneous device of claim 1, 6 or 7 wherein:

said retention platform further comprises a central portion and a platform body having an outer edge surface; and, said outer edge surface is concentric with said retention platform central portion.

\* \* \* \* \*